United States Patent [19]

Sleighter

[11] 4,358,305

[45] Nov. 9, 1982

[54] METHOD OF AND APPARATUS FOR ANALYZING ATMOSPHERE OF A COMBUSTION CHAMBER

[75] Inventor: George E. Sleighter, Natrona Heights, Pa.

[73] Assignee: PPG Industries, Inc., Pittsburgh, Pa.

[21] Appl. No.: 304,538

[22] Filed: Sep. 23, 1981

[51] Int. Cl.³ .......................... C03B 5/16; C03B 5/24
[52] U.S. Cl. .......................................... 65/29; 65/158; 65/161; 65/DIG. 13; 23/230 A; 73/23; 422/62; 422/111; 432/23; 432/30; 432/182
[58] Field of Search .......... 65/29, 161, 158, DIG. 13; 432/181, 182, 183, 28, 30, 23; 23/230 A; 422/62, 111; 73/23

[56] References Cited

U.S. PATENT DOCUMENTS

| | | | |
|---|---|---|---|
| 3,218,842 | 11/1965 | Ludwig et al. | 73/23 |
| 3,515,529 | 6/1970 | Love et al. | 65/356 X |
| 3,759,087 | 9/1973 | Iwao et al. | 73/23 |
| 3,856,496 | 12/1974 | Nesbitt et al. | 65/29 |
| 3,954,433 | 5/1976 | Holler | 65/29 |
| 4,313,722 | 2/1982 | Yigdall | 432/28 X |

Primary Examiner—Robert L. Lindsay, Jr.
Attorney, Agent, or Firm—Donald Carl Lepiane

[57] ABSTRACT

A hole through each of opposed walls of a combustion chamber of a glass melting apparatus and piping interconnect the chamber atmosphere to an oxygen analyzer. A sample of the chamber atmosphere is continuously moved through each of the holes and piping to the analyzer by the biasing action of the positive pressure differential between the chamber atmosphere and the ambient atmosphere.

10 Claims, 5 Drawing Figures

METHOD OF AND APPARATUS FOR ANALYZING ATMOSPHERE OF A COMBUSTION CHAMBER

BACKGROUND OF THE INVENTION

1. Field of the Invention

This invention relates to a method of and apparatus for analyzing, e.g., measuring oxygen contact in the atmosphere of a combustion chamber, such as the type used for melting and/or fining glass.

2. Discussion of the Technical Problems

In the process of making a continuous flat glass ribbon, glass batch materials are conveniently moved into the upstream end of a heated combustion chamber. As the batch materials move downstream through the heated chamber, they melt to provide a pool of molten glass. The molten glass, as it advances through the heated chamber, is fined and the fined molten glass is continuously and controllably fed onto a pool of molten metal contained in a heated forming chamber. The molten glass, as it advances through the forming chamber, is controllably cooled and acted on to exit the forming chamber as a continuous glass ribbon of a given thickness and width.

The combustion chamber usually includes a regenerator at each of opposed chamber walls. The regenerators are usually elongated corridors which communicate with the chamber interior by way of a plurality of spaced ports in each of the opposed chamber walls. The interior of the regenerators usually includes a stacked arrangement of bricks, sometimes called "checker packing," which are heated by hot exhaust gases passing through the ports at one chamber wall and over the checker packing during one half of a heating cycle. During the remaining half of the heating cycle, combustion air passes over the heated checker packing through the ports past a fuel pipe mounted at the mouth of each port. The heated combustion air and combustion fuel from the pipes mix which results in flames issuing from the side of the chamber toward the chamber interior to heat same. With the above arrangement, as the packing of a regenerator at one side of the chamber is absorbing heat from the exhaust gases during one half of a heating cycle, the packing of the regenerator at the other side is heating incoming combustion air.

To maintain a high combustion efficiency and a chemical balance in the molten glass, the furnace atmosphere is monitored. In this regard, the exhaust gas is monitored to determine the percent of oxygen content therein. If the percent of oxygen contact in the chamber is above a predetermined level, the combustion may be considered to be incomplete, e.g., insufficient fuel moving through the fuel pipes, and if the oxygen content is below the predetermined level, there may be too much fuel moving through the fuel pipe resulting in wasting unignited fuel. In addition to monitoring oxygen content of the chamber atmosphere to determine combustion efficiency, oxygen content in the chamber atmosphere is also monitored because it can affect the fining process. For example, excess oxygen can cause excessive bubbles in the fined molten glass which results in excess voids in the formed glass ribbon. In addition, oxygen partial pressure in the chamber can affect the color of the formed glass ribbon. By way of illustration, oxygen partial pressure may be controlled to prevent undesirable oxidation of the iron or reduction of the iron or sulfur in the molten glass which can result in a yellowish green colored glass ribbon, a bluish tint in the glass ribbon, or an amber colored glass ribbon.

At present, there are available probes for monitoring oxygen content in the combustion chamber. One such probe is taught in U.S. patent application Ser. No. 227,015, filed on Jan. 21, 1981, in the names of E. P. Savolskis and T. L. Sanders, for "ATMOSPHERE SENSING DEVICE FOR A FURNACE" now U.S. Pat. No. 4,338,117, granted July 6, 1982. Although the probe is acceptable, there are limitations. For example, it is taught to mount the probe through a regenerator wall adjacent a port and above the checker packing to analyze the exhaust gases. However, in this position, the probe is mounted in an area of negative pressure relative to the pressure of the ambient atmosphere. This results in drawing air from the furnace exterior through openings, e.g., cracks in the port or regenerator walls which can dilute the sample of chamber atmosphere being analyzed.

As can now be appreciated, it would be advantageous to provide a method of and apparatus for sensing oxygen content in the atmosphere of a glass melting and/or fining furnace of a flat glass melting apparatus that eliminates the limitations of the presently available techniques.

SUMMARY OF THE INVENTION

This invention relates to a method of monitoring atmosphere of a combustion chamber having a regenerator at each of opposed chamber walls. The chamber may be used to melt glass batch materials and/or to fine molten glass and may be of the type used in making a continuous flat glass ribbon. Each regenerator communicates with chamber interior through at least one port and the pressure differential between the atmosphere at the chamber interior and ambient atmosphere is positive. The method includes the steps of providing at least one access hole through each of the opposed chamber walls to move under the biasing force of the positive pressure differential a portion of the chamber atmosphere defined as a sample, through each of the at least one access holes. Thereafter, the sample is analyzed to monitor the chamber atmosphere, e.g., determine percent oxygen content or percent combustion products in the chamber atmosphere for subsequent control of oxygen content or of combustion reactants, respectively, in the chamber atmosphere.

This invention also relates to a monitoring apparatus that may be used to practice the above method.

The instant invention eliminates the problems associated with monitoring samples of the chamber atmosphere at locations where pressure differential between the chamber atmosphere and ambient atmosphere is negative. More particularly, at these negative pressure differential locations, the ambient atmosphere, e.g., air is pulled through cracks in the port or regenerator walls and uncontrollably dilutes the sample i.e., the sample has a higher percentage of oxygen due to the mixing of the sample with the ambient atmosphere. By taking samples at positive pressure differential locations, the positive pressure prevents the ingress of the ambient atmosphere thereby preventing dilution of the sample being analyzed.

DESCRIPTION OF THE INVENTION

Figure 2:
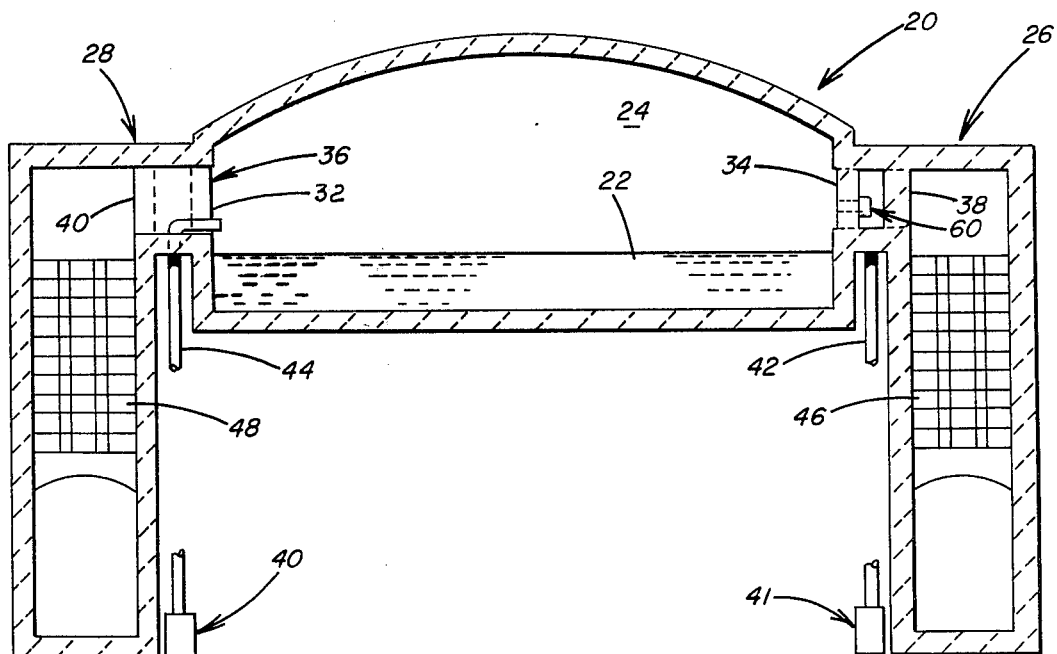
FIG. 2 is a view taken along lines 2—2 of FIG. 1 with the roof added.
Figure 1:
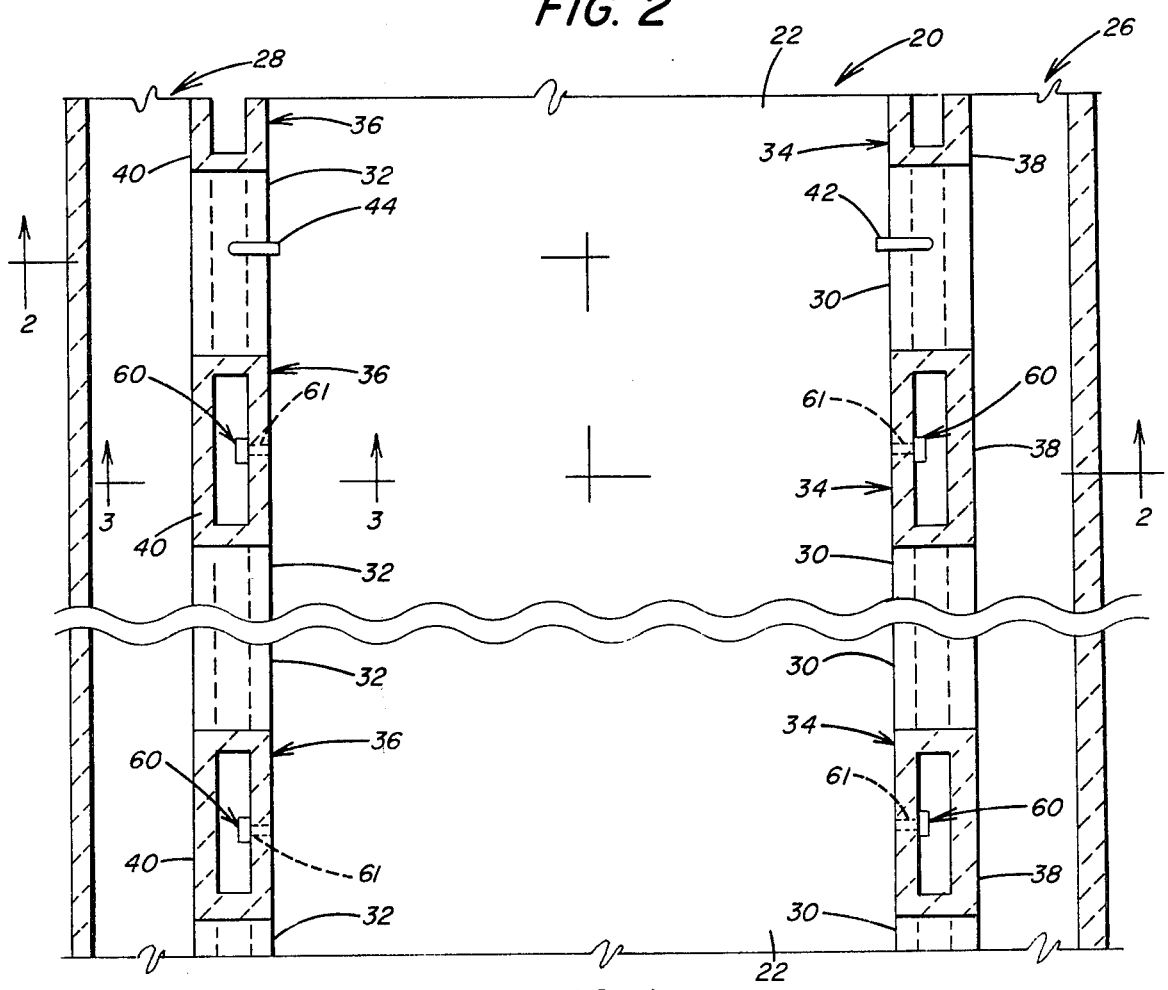
FIG. 1 is a sectional plan view of a glass melting and/or fining furnace incorporating features of the invention of a glass making apparatus having the roof removed for purposes of clarity.

The regenerative furnace arrangement 20 shown in FIGS. 1 and 2 is typical of a melting furnace used in the flat glass industry. It should be understood that such a furnace is being described as an illustrative example, and that the invention is applicable to regenerative furnaces, recuperators, regenerators of other types and/or furnaces. As shown in FIG. 2, a pool of molten and/or partially melted glass 22 is contained in melting zone 24 which also serves as a combustion chamber. Regenerators 26 and 28 flank the combustion chamber 24 and communicate therewith by a plurality of ports 30 and 32, respectively. Adjacent ports 30 or 32 are spaced from one another by an inner furnace wall 34 or 36, respectively, usually referred to as a "breast wall" and an outer furnace wall 38 or 40, respectively. With reference to FIGS. 1 and 2 as required, fuel for combustion is conveniently and controllably moved for supply 41 into and through pipe 42 or 44. Air for combustion passes upwardly through one of the regenerators 26 or 28 where it is preheated by passing over a hot refractory brick checker packing 46 or 48. The heated combustion air moves through port 30 or 32 where it combines with fuel emanating from the pipes 42 or 44, respectively, at the mouth of the port. Flames from the ignition of the combustion fuel issue a considerable distance into the combustion chamber 24 and resultant hot exhaust gases pass through the port 32 or 30 into the opposite regenerator 28 or 26. The exhaust gases, as they move the regenerator 28 or 26, heat the checker packing 48 or 46, respectively. A complete discussion of a regenerative furnace of a flat glass making apparatus is discussed in U.S. Pat. No. 4,047,560 which teachings are hereby incorporated by reference.

Figure 3:
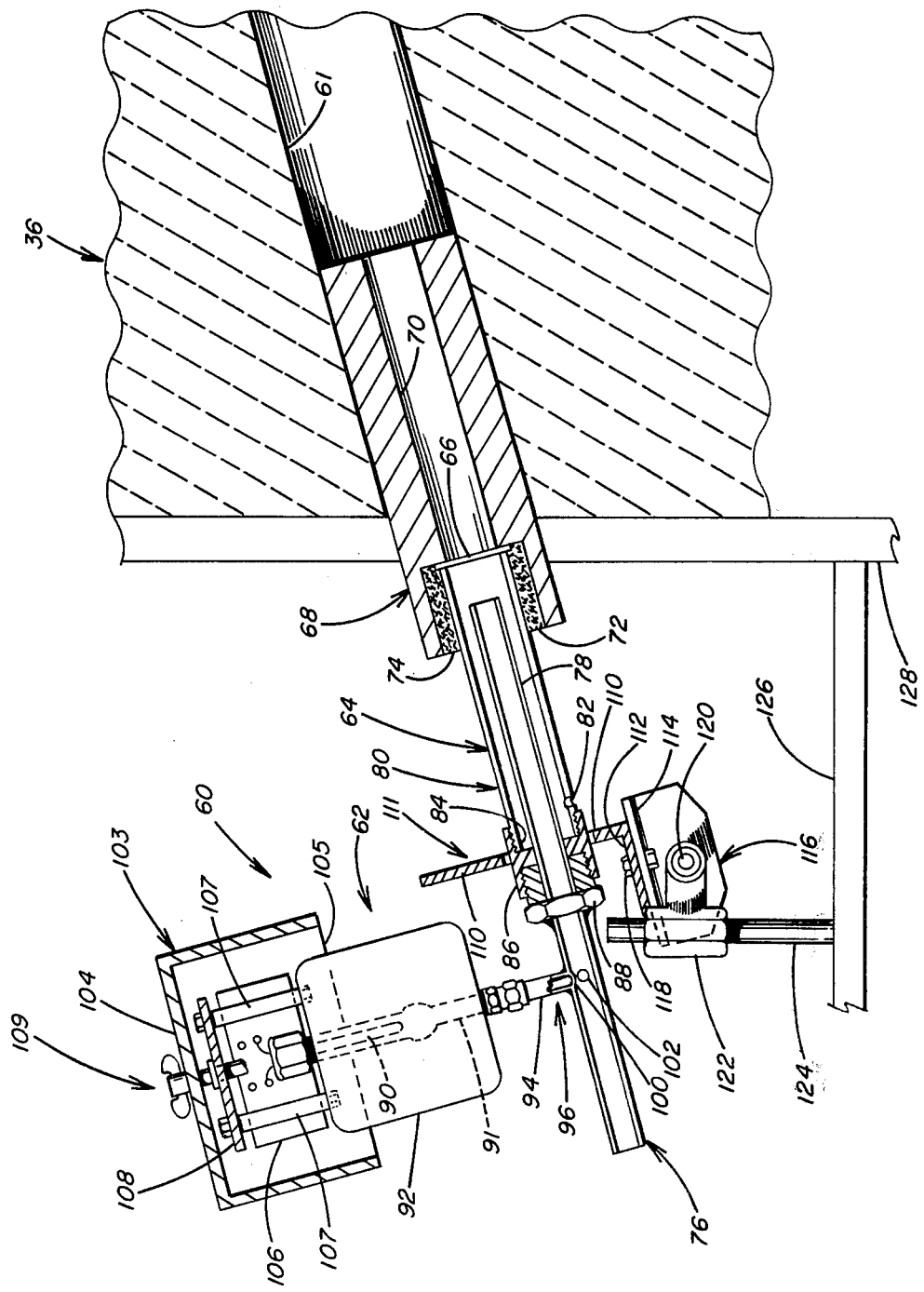
FIG. 3 is a view taken along lines 3—3 of FIG. 1 and having portions removed for purposes of clarity.
Figure 4:
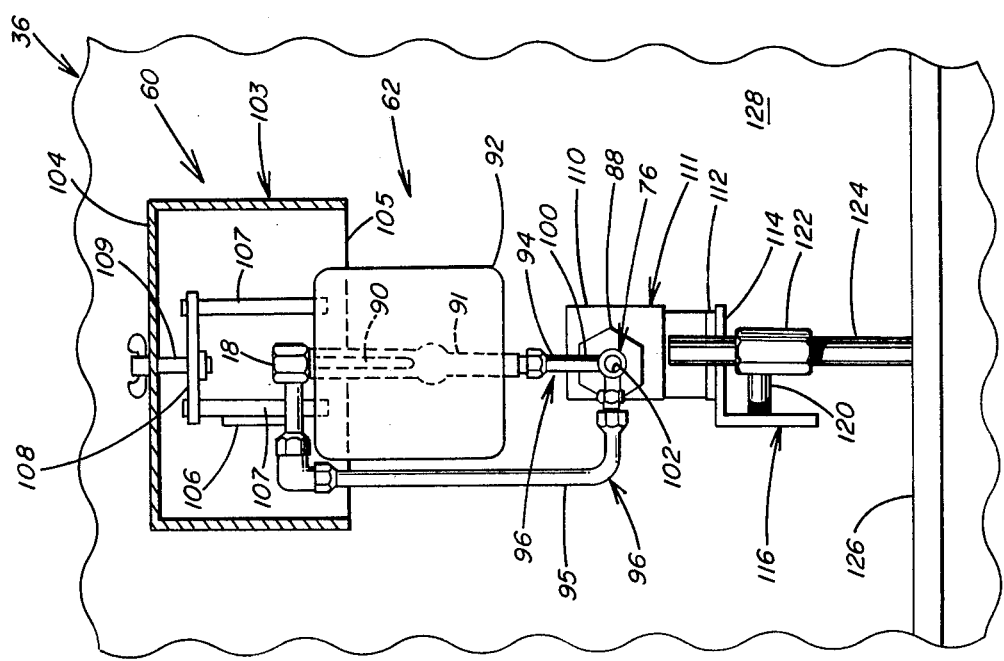
FIG. 4 is an end view of FIG. 3 and having portions removed for purposes of clarity.

Referring also to FIG. 3, mounted in the breast wall 34 and 36 is a sensing apparatus 60 incorporating features of the invention for analyzing, e.g., determining oxygen contents in the atmosphere of the combustion chamber by analyzing a sample of the atmosphere passing through hole 61 in the breast wall 36. With reference to FIGS. 3 and 4 as required, the sensing apparatus 60 includes a gas analyzing assembly 62 connected to open ended conduit 64 having its end 66 mounted in adaptor block 68 which is partially mounted in the wall hole 61. The adaptor block 68 is preferably made of a material capable of withstanding the elevated temperatures of the chamber atmosphere, e.g., temperatures of up to or greater than about 2552° F. (1400° C.). Although not limiting to the invention, the invention is practiced using an adaptor block made of a ceramic refractory, such as beta alumina sold under the trademark Monofrax ® and having a square cross-section with each side having a length of about 2.5 inches (6.5 centimeters) and a length of about 6 inches (15.24 centimeters). The block 68 has a ½ inch (1.27 centimeter) diameter bore 70 and 1½ inches (3.71 centimeters) counterbore 72 for receiving the end 66 of the conduit 64.

Packing 74, e.g., refractory fibers of the type sold by Babcock-Wilcox of New York, are packed around the conduit end 66 in the counterbore 72 to assist in directing the sample of chamber atmosphere into the conduit 64. the conduit 64 includes an open ended pipe 76 which is sized to pass the sample of the chamber atmosphere and made of a material capable of withstanding the temperature and chemistry of the furnace atmosphere with minimal deterioration. Although not limiting to the invention, the invention is practiced using a stainless steel pipe 76 having a length of about 1 foot (0.3 meter), a wall thickness of about 1/16 inch (0.16 centimeter) and an inside diameter of about ½ inch (1.27 centimeters). Pipe portion 78 adjacent the adaptor block 68 is preferably and conveniently mounted in a sleeve 80, e.g., 1½ inches (3.71 centimeters) schedule 40 stainless steel pipe. The sleeve 80 having the end 66 in the block 68 reduces heat loss of the sample as it moves through the pipe portion 78. A hole 82 in the sleeve 80 provides for gas escape and to remove any condensates that may form in the sleeve 80. The pipe portion 78 is secured in the sleeve in any convenient manner, e.g., by threading sleeve end 84 into end of an internally threaded collar 86 and threading a reducer 88 having the pipe 76 therein into the other end of the collar 86 to secure the pipe 78 in position.

The analyzing assembly 62 is not limiting to the invention and any convenient type for analyzing a gas sample may be used in the practice of the invention. The invention is practiced using an oxygen sensor cell 90 mounted in cell housing 91 which is mounted in oven 92. The cell housing 91 is connected at one end to convection loop portion 94 and at the other end to convection loop portion 95 of convection loop 96. The other end of the convection loop portion 94 is connected at 100, i.e., ingress hole 100 to the pipe 76 and the other end of the convection loop portion 95 is connected at 102, i.e., egress hole 102 to the pipe 76. Although not limiting to the invention, the ingress hole 100 and egress hole 102 are adjacent one another to minimize pressure difference between the gas sample flowing into and out of the convection loop 95 and the cell housing 91 so that the heated sample moves past the sensor cell 90 by convection. The sensor 90 used in the practice of the invention is of the type sold by Thermox Company, Type WDG-GT and is preferably mounted in the oven 92 to maintain the sensor cell 90 at a constant temperature for the gas being analyzed, e.g., at 1418° F. (770° C.) for oxygen and 1500° F. (812° C.) for combustible exhaust gases.

A dust cover 103 having a closed top end 104 and open bottom end 105 is preferably mounted over the upper portion of the oven 92 as viewed in FIGS. 3 and 4 to protect terminal board 106 which provides electrical control and access as required for the oven 92 and sensor cell 90. The dust cover 103 has the open bottom end 105 to provide for the movement of ambient air. The percent of oxygen in the ambient air is used as a reference value for the oxygen sensor cell 90. The dust cover 103 is supported over the oven 92 in any convenient manner. For example, and as shown in FIGS. 3 and 4, three spaced posts 107 each have one end secured to the oven 92 and a plate member 108 secured to their opposite end. A wing nut assembly 109 mounted to the plate member 108 passes through and is secured in the closed top end 104 of the dust cover 103.

The sensing apparatus is secured in position in any convenient manner. For example, and with continued reference to FIGS. 3 and 4, the collar 86 is mounted in leg 110 of an angle iron 111 with other leg 112 secured to leg 114 of angle iron 116 by bolt assembly 118. The angle iron 116 is secured to pipe 120 rotatably mounted and secured in pipe collar 122 which is rotatably mounted and secured on pipe 124. The pipe 124, in turn, is mounted on rigid member 126 secured to the superstructure 128 of the chamber 20. As can now be apprciated, the invention is not limiting to the relationship of the conduit 64 and the breast wall 34 or 36. For example, the longitudinal axis of the conduit 64 is sloped relative to the vertical plane of the breast wall as shown in FIG. 3; however, the longitudinal axis of the conduit 64 may be normal thereto.

In the practice of the invention for monitoring oxygen content of the chamber atmosphere, portions, e.g., continuous portions, of the furnace atmosphere defined as a sample move under pressure into and through the hole 61 in the breast wall 34 and 36. In general, the pressure differential between the chamber atmosphere or interior and the ambient atmosphere or chamber exterior is greater than about 0.001 inch (0.0254 millimeter) of water. The sample moves through the wall hole 61, through the adaptor bore 70 into the end 66 of the conduit 64. A portion of the sample moves through the sleeve 80 and out of the sleeve hole 82 and a portion of the sample flows into the pipe portion 78 and moves through the pipe 76. Prior to exiting the pipe 76, a portion of the sample moves into the ingress hole 100 through the convection loop 96 and cell housing 91 and out of the convection loop by way of egress hole 102. The sensor cell 90 analyzes the sample passing therethrough for oxygen content. If the oxygen content as determined by the sensor cell 90 is low, e.g., indicating the excess fuel is being moved through the pipe 42 or 44, the fuel supply 41 is adjusted to reduce the fuel input.

Figure 5:
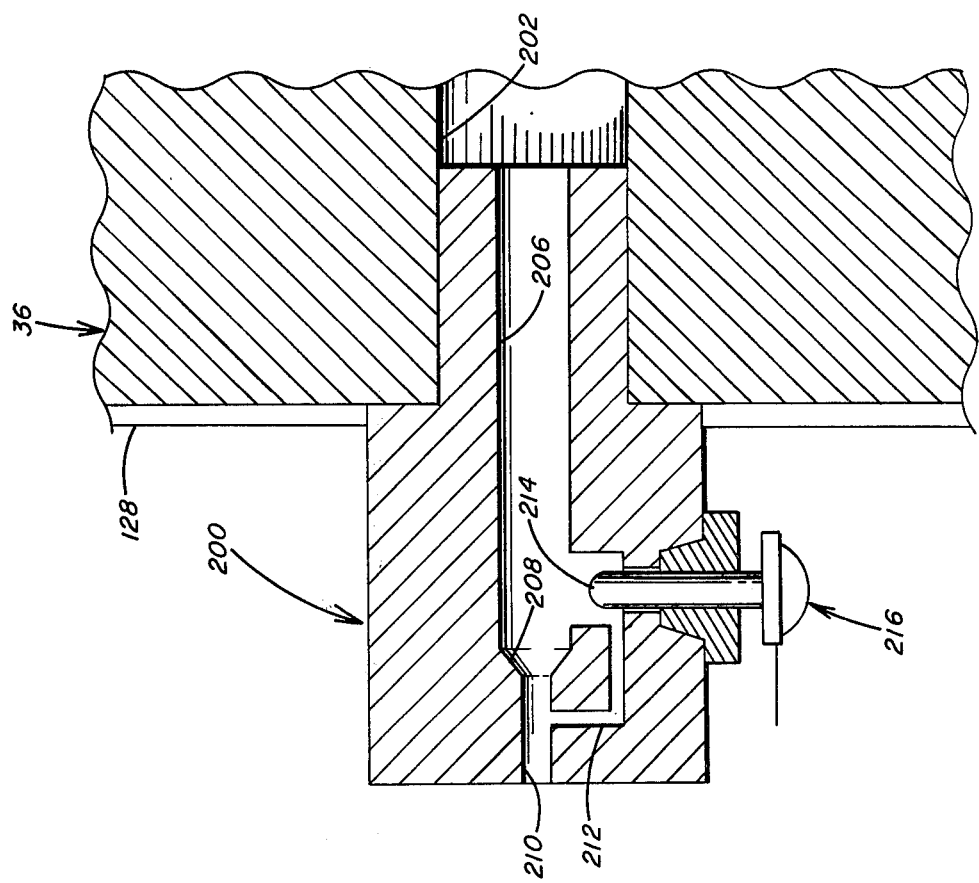
FIG. 5 is a view similar to the view of FIG. 3 illustrating another embodiment of the invention.

Shown in FIG. 5 is another embodiment of the invention that includes an adaptor block 200 mounted in hole 202 formed in the breast wall 36 of the combustion chamber 20. The adaptor block 200 has a first main passageway 206 necked down at 208 into a second smaller main passageway 210 with the passageways 206 and 208 interconnected by intermediate or ancillary passageway 212. Mounted in the adaptor block 200 at the junction of the first main passageway 206 and intermediate passageway 212 is sensing end 214 of oxygen sensor 216, e.g., a Zirconia cell oxygen sensor of the type sold by Corning Glass Works, Corning, N.Y.

In practice, the positive pressure in the chamber moves a sample of the chamber atmosphere through the hole 202 in the breast wall 36 or 34 into the first main passageway 206. The necked down portion at 208 causes a back pressure to direct a portion of the sample through the interconnecting passageway 212 over the sensor end 214 as the remaining portion of the sample moves into the second main passageway 210 as does the sample flowing from the interconnecting passageway 212. The sample thereafter flows out of the adaptor block 200.

As can now be appreciated, the invention is not limited to the above examples which were presented for illustration purposes only. For example, the chamber sample may be analyzed for percent oxygen content to determine level of oxidation and/or reduction of the iron or sulfur in the molten glass. If the oxygen content as indicated by the sample is too high, the fuel input may be increased, and vice versa.

What is claimed is:

1. A method of monitoring atmosphere of a combustion chamber having a regenerator at each of opposed chamber walls with each regenerator communicating with chamber interior by at least one port, wherein pressure differential between chamber atmosphere and ambient atmosphere is positive, comprising the steps of:
   providing at least one access hole through each of the opposed chamber walls to move under the biasing force of the positive pressure differential a portion of the chamber atmosphere defined as a sample through each of the at least one access holes;
   determining oxygen content in the sample; and
   controlling oxygen content in the chamber atmosphere in response to said determining step.

2. A method of monitoring atmosphere of a combustion chamber having a regenerator at each of opposed chamber walls with each regenerator communicating with chamber interior by at least one port, wherein pressure differential between chamber atmosphere and ambient atmosphere is positive, comprising the steps of:
   providing at least one access hole through each of the opposed chamber walls to move under the biasing force of the positive pressure differential a portion of the chamber atmosphere defined as a sample through each of the at least one access holes;
   determining combustion products in the sample; and
   controlling combustion reactants in response to said determining step.

3. The method as set forth in claim 1 or 2 wherein glass making materials are melted in the chamber.

4. The method as set forth in claim 1 or 2 wherein molten glass is fined in the chamber.

5. An apparatus for monitoring atmosphere of a furnace including a combustion chamber; regenerating means at each of a pair of opposed chamber walls; and at least one port at each of the opposed chamber walls to provide communication between the regenerating means and chamber interior wherein during furnace operation the pressure differential between the chamber atmosphere and ambient atmosphere is positive, comprising:
   means mounted at each of the opposed chamber walls for passing a portion of the chamber atmosphere defined as a sample from the chamber interior to the chamber exterior, said passing means includes the positive pressure differential and at least one hole through each of the opposed chamber walls;
   means for analyzing oxygen content in the sample;
   means for interconnecting said passing means and said analyzing means; and
   means fors controlling oxygen content in the chamber in response to said analyzing means.

6. The apparatus as set forth in claim 5 wherein said interconnecting means includes:
   a block having a main passageway extending between and through ends of the block with a portion of said passageway adjacent one end of said block having a cross-sectional area greater than cross-sectional of adjacent portion of the main passageway and an ancillary passageway interconnecting the two adjacent passageway portions; and
   means for mounting said analyzing means in said block to act on sample passing through said ancillary passageway.

7. The apparatus as set forth in claim 5 wherein said interconnecting means includes:
   an adaptor having a passageway extending between and through ends of said adaptor;

an outer sheath having one end mounted in an end of said block;

a convection pipe loop having a gas entrance end and a gas exit end to move the sample to be analyzed past said analyzing means; and a pipe having an end portion secured in said sheath and opposite end portion interconnected to said ends of said convection loop.

8. An apparatus for monitoring atmosphere of a furnace including a combustion chamber; regenerating means at each of a pair of opposed chamber walls; and at least one port at each of the opposed chamber walls to provide communication between the regenerating means and chamber interior wherein during furnace operation the pressure differential between the chamber atmosphere and ambient atmosphere is positive, comprising:

means mounted at each of opposed chamber walls for passing a portion of the chamber atmosphere defined as a sample from the chambers interior to the chamber exterior, said passing means includes the positive pressure differential and at least one hole through each of the opposed chamber walls;

means for analyzing combustion products in the sample;

means for interconnecting said passing means and said analyzing means; and means for controlling input of combustion reactants into the chamber in response to said analyzing means.

9. The apparatus as set forth in claim 5 or 8 wherein the chamber includes a glass melting section for providing molten glass.

10. The apparatus as set forth in claim 5 or 8 wherein the chamber includes a section for fining molten glass.

* * * * *

UNITED STATES PATENT AND TRADEMARK OFFICE
CERTIFICATE OF CORRECTION

PATENT NO. : 4,358,305

DATED : November 9, 1982

INVENTOR(S) : George E. Sleighter

It is certified that error appears in the above-identified patent and that said Letters Patent are hereby corrected as shown below:

Claim 5, Column 6, Line 51, "fors" should be --for--.

Claim 8, Column 8, Line 3, "chambers" should be --chamber--.

Signed and Sealed this

Eighth Day of February 1983

[SEAL]

Attest:

GERALD J. MOSSINGHOFF

Attesting Officer

Commissioner of Patents and Trademarks